(12) United States Patent
Frey

(10) Patent No.: US 7,867,188 B2
(45) Date of Patent: Jan. 11, 2011

(54) SYSTEM AND DISPOSABLE FOR DIRECT HEATING FOR INFUSATE AND INTRAVENOUS FLUIDS AND A METHOD THEREFOR

(75) Inventor: William E. Frey, Kindston, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 899 days.

(21) Appl. No.: 11/432,393

(22) Filed: May 12, 2006

(65) Prior Publication Data
US 2007/0265689 A1 Nov. 15, 2007

(51) Int. Cl.
*A61N 1/30* (2006.01)
*A61F 7/00* (2006.01)
*A61F 7/12* (2006.01)

(52) U.S. Cl. .......................... 604/19; 607/105; 607/113
(58) Field of Classification Search ..................... 604/19
See application file for complete search history.

(56) References Cited

U.S. PATENT DOCUMENTS

| 4,532,414 A | 7/1985 | Shah et al. | |
| 5,063,994 A | 11/1991 | Verkaart | |
| 5,180,896 A * | 1/1993 | Gibby et al. | 219/687 |
| 5,653,692 A * | 8/1997 | Masterson et al. | 604/113 |
| 6,076,962 A | 6/2000 | Chen | |
| 6,142,974 A | 11/2000 | Kistner et al. | |
| 6,146,359 A * | 11/2000 | Carr et al. | 604/114 |
| 6,744,027 B2 | 6/2004 | Fathi et al. | |
| 2001/0053525 A1* | 12/2001 | Chu | 435/6 |
| 2002/0095198 A1* | 7/2002 | Whitebook et al. | 607/100 |
| 2003/0155669 A1* | 8/2003 | Bronshtein et al. | 264/4.1 |
| 2005/0008354 A1 | 1/2005 | Cassidy | |
| 2005/0089319 A1* | 4/2005 | Mitsunaga et al. | 392/467 |

* cited by examiner

*Primary Examiner*—Nicholas D Lucchesi
*Assistant Examiner*—Jason Flick
(74) *Attorney, Agent, or Firm*—Louis Woo

(57) ABSTRACT

A disposable warmer cartridge is used to heat fluids to be infused to the patient to prevent hypothermia in the patient. The cartridge has in its chamber a pair of spaced in parallel electrodes that have substantially the same dimension. When RF power is fed to the electrodes, an alternating electric field is generated between the electrodes to directly heat the fluid that is in the chamber. The heating of the fluid is achieved in a substantially instantaneous manner by controlling the energization of the electrodes through the distributed impedance of the electric field between the electrodes. Heat is readily controlled by modulating the RF power fed to the electrodes. Feedback to control the temperature of the fluid in the cartridge may be provided by non-contact and direct contact sensor(s).

30 Claims, 17 Drawing Sheets

SYSTEM AND DISPOSABLE FOR DIRECT HEATING FOR INFUSATE AND INTRAVENOUS FLUIDS AND A METHOD THEREFOR

FIELD OF THE INVENTION

The present invention relates to a fluid warming system used to prevent hypothermia in a patient, and in particular a system and a disposable heater lumen used in the system to heat the fluid fed thereto. The invention moreover relates to the use of radio frequency energy for directly heating the fluid in the heater lumen.

BACKGROUND OF THE INVENTION

Published research has correlated significant adverse consequences such as impaired wound healing, adverse cardiac events, altered drug metabolism, and coagulopathies with unplanned perioptive hypothermia. With prevention, and management of hypothermia, patients also experience a greater level of comfort, and avoid postoperative shivering and the unpleasant sensation of feeling cold.

The warming of infusate or intravenous (IV) fluids to prevent hypothermia in the current state of the art is accomplished by many varied systems. One such system, the Ranger Fluid Warmer from Arizant Healthcare, uses two heated plates with bladder-like plastic membrane containing a serpentine fluid path held between the plates to heat the infusate through the bladder wall by contact heat transfer. A second such system is disclosed in U.S. Pat. No. 4,532,414. The '414 system uses a box-like enclosure that contains a heated plate with a serpentine groove into which an infusate lumen or conduit is placed. When the box is closed, the infusate is heated by heat transfer from the warm plate through the lumen wall. A third such system is disclosed in U.S. Pat. No. 5,063,994 assigned to the assignee of the instant invention. The '994 system uses a triple lumen tube with warm water being circulated through the two outer lumens to warm the infusate in the central lumen through heat transfer. These systems are all heat transfer systems whereby various types of heat exchangers are used with disposable heat exchanging mediums.

The heat exchanger type infusate warmers in the prior art all have a common drawback. This is because heat exchangers, as their name implies, exchange heat through a heat exchange medium. Thus, there is a time lag in the heat being transferred from the heating element to the infusate or fluid (and removed therefrom), as there is a partition in the form of a wall or membrane that separates the heating element and the medium that is being heated and which tends to stay warm even after it is no loner being heated by the heating element. A need therefore exists for a system that can provide substantially instantaneous control of the heating of an infusate or intravenous fluids.

SUMMARY OF THE PRESENT INVENTION

The instant invention warms the infusate medium by direct means without a heat exchanger to provide normothermic fluid to the patient. Infusate in a slow flow, gravity feed system is generally 0.9% saline. An infusate used may be, but is not limited to, packed red blood cells (RBCs). The general property of all of the infusate and fluids being infused to a patient is that they are electrically conductive electrolytes.

Radio frequency (RF) energy is a form of electromagnetic energy in which rapidly oscillating electromagnetic fields cause movement of charged particles. It is the inventor's intent that an infusate or electrolyte fluids be heated by RF energy. Under the direct excitation of RF energy, the resultant molecular motion of the molecules in the electrolytic fluids would generate heat. The RF frequency excitation range could be, but not limited to, approximately 400 KHz to 2 MHz.

Another aspect of this invention is that the RF heater and the disposable lumen may be one and the same.

The disposable heater lumen may be a warmer cartridge with proper intravenous fluid connections. Two of the inside opposing walls of the warmer have fully conductive metal surfaces facing each other that protrude beyond a permanent seal either on the end of the warmer for a single infrared (IR) configuration embodiment, or a side of the warmer for a multiple IR configuration embodiment. Electrical RF heating may be internal and RF power connections may be external. When RF energy is applied to the electrodes, the fluid heats. The RF power may be controlled by modulation much in the same way as resistance heating. When RF power is removed, all heating stops instantly. The only thermal mass would be in the electrodes and the residual within the walls of the cartridge, neither of which would be warmer than the fluid within the warmer. If there is no fluid, there is no conduction and no heat is produced.

Closed loop temperature management or feedback control of the temperature for the inventive heater may be achieved with either non-contact or contact sensor means. One or more infrared (IR) sensors may be used for providing a non-contact temperature feedback, while one or more direct contact thermistors or RTDs (Resistance Temperature Detectors) may be employed for providing a contact temperature feedback.

The use of two temperature sensors of any type, one at the inlet side and one at the outlet side of the warmer cartridge, allows the temperature to be controlled by either sensor, whichever senses a higher temperature. Over-temperature safety may also be controlled by either one of the sensors that senses the preset higher temperature. As fluid flows, the outlet temperature will exceed the inlet temperature under applied RF power. As the fluid stops, the respective temperatures measured by both sensors will approach the same value, or may even reverse due to convection flow if the inlet port is above the outlet port. With the direct contact type sensor, if air enters the inlet luer of the warmer, the sensor that becomes air-bound would increase in temperature due to the sensor's self-heating characteristic and could be used as a "safety valve" to disconnect power to the heater and to alert the operator.

For the non-contact sensor method, thermopile type infrared sensors capable of measuring in the 5.5 um area of the spectrum may be used. These sensors are similar to those currently used in the IR ear thermometers, although thermistor type IR sensors may also be used. The sensor(s) view the fluid through the wall of the warmer at an area of reduced thickness.

The present invention therefore relates to an apparatus, or a system for warming infusate or intravenous fluids for use by a patient. The apparatus includes a radio frequency (RF) generator that is capable of outputting a RF energy, a fluid reservoir or store, a body having a chamber including an inlet and an outlet, a fluid from the fluid store for treatment of the patient passing into the chamber though the inlet and out of the chamber through the outlet. There is at least one pair of spaced apart electrodes or conductive surfaces in the chamber electrically connected to the RF generator, so that the electrodes may be selectively powered by RF energy from the RF generator for effecting an electric field between the electrodes to heat the fluid in or passing through the chamber. The apparatus of the instant invention further includes a temperature regulating system communicatively connected to the body for sensing the temperature of the fluid in the chamber and for controlling the RF energy supplied to the electrodes to maintain the fluid in the chamber at a desired temperature. Each of the electrodes may be a layer or a sheet of conductive metal attached to opposing surfaces of the chamber. Instead of layers being attached to the opposing surfaces, metallic conductive materials may be deposited onto opposing surfaces of the chamber so as to form two parallel, or substantially parallel, conductive planes to which RF energy may be supplied for establishing an alternating electric field therebetween. The inventor further envisions that some portions of the spaced apart electrodes may not need to be spaced in parallel, as for example at either the distal and/or proximal portions where the fluid is input into and output from the chamber.

The instant invention also relates to a disposable warmer for heating fluids to be infused to a patient that comprises a body having a chamber with an inlet and an outlet for accepting fluid, the body being non-permanently connected to a fluid store at its inlet to enable the fluid in the fluid store to flow into the chamber and non-permanently connectable to a conduit at its outlet to supply the fluid to the patient. There is further provided in the warmer at least one pair of electrodes having substantially the same dimension that may be spaced substantially in parallel. These electrodes are adapted to be electrically energized by RF energy from an RF generator so that a substantially evenly distributed alternating electric field is established between the electrodes for heating the fluid in the chamber along the length of the chamber.

The instant invention moreover relates to a method of infusing a temperature controlled fluid to a patient to prevent hypothermia in the patient. The method includes the steps of: (a) forming a body having a chamber with an inlet and an outlet; (b) spacing substantially in parallel in the chamber at least one pair of electrodes; (c) electrically connecting the electrodes to an RF generator; (d) connecting the inlet of the body to an output of a fluid store that contains a fluid to be infused to the patient so as to enable the fluid in the fluid store to flow into the chamber; (e) supplying from the RF generator a radio frequency energy to the electrodes to effect an alternating electric field between the electrodes to heat the fluid in the chambers; and (f) connecting the outlet of the body to a conduit in fluid communication with the patient so that the fluid heated in the chamber may be output to the patient.

BRIEF DESCRIPTION OF THE FIGURES

The invention is best understood by reference to the following description taken in conjunction with the accompanying drawings, wherein.

DETAILED DESCRIPTION OF THE INVENTION

Figure 1:
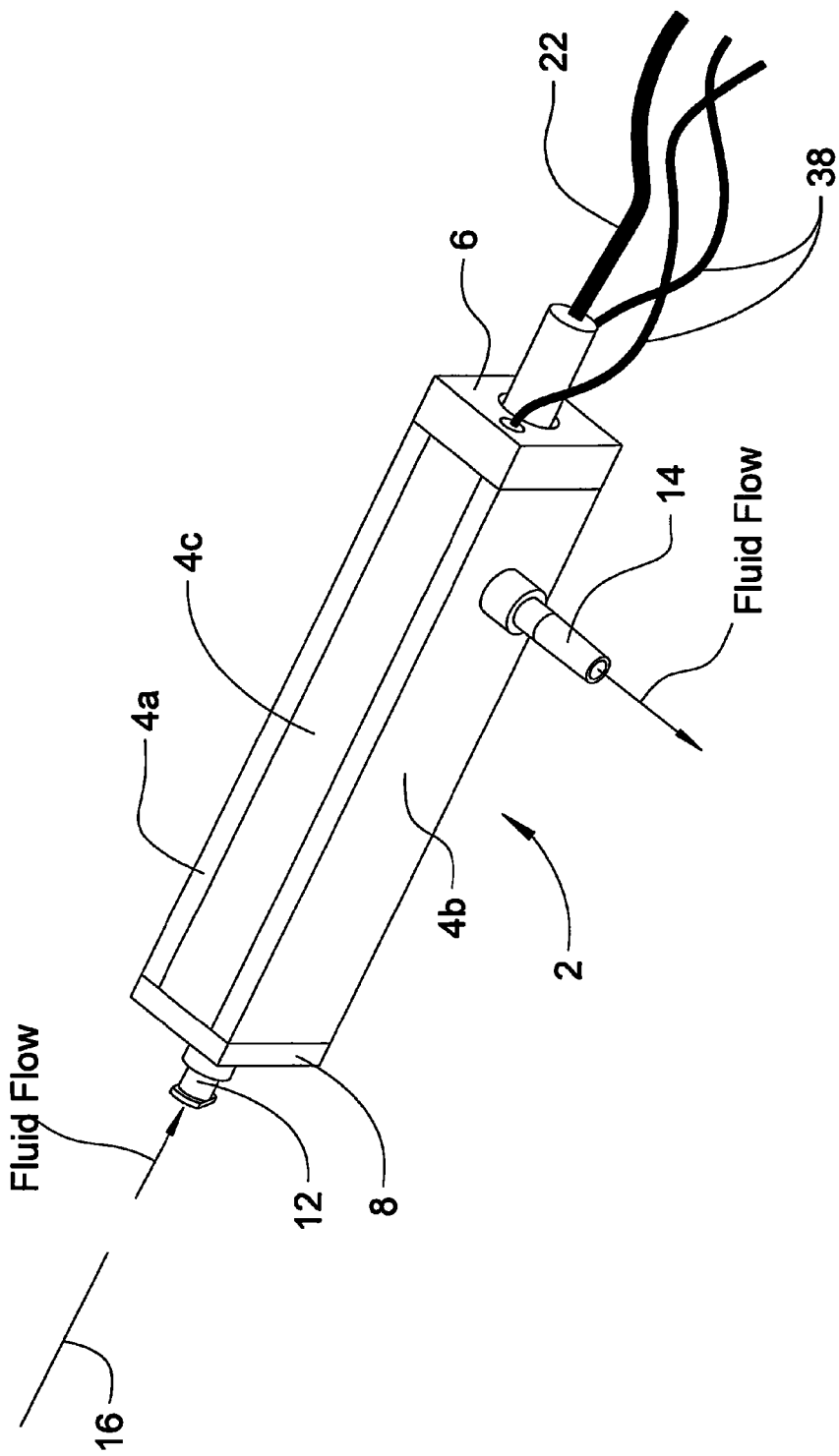
FIG. 1 is a perspective view of the disposable warmer cartridge of the instant invention.
Figure 2:
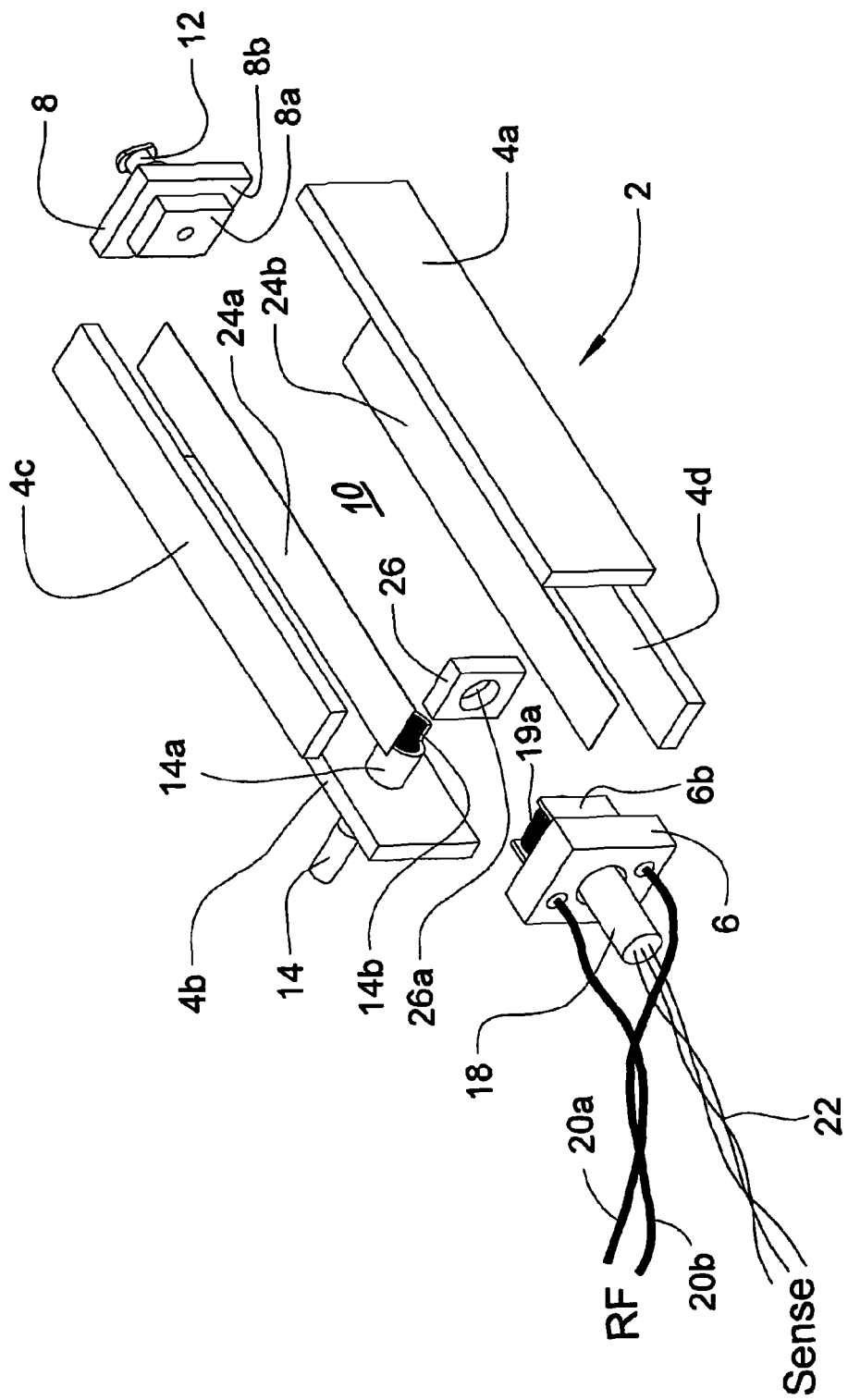
FIG. 2 is an exploded view of the various components of the inventive warmer cartridge.

With reference to FIGS. 1 and 2, a disposable warmer or lumen in the form of a cartridge is shown. In particular, cartridge 2 has an elongate body 4 that has four sidewalls 4a-4d. Two end caps 6 and 8 which, together with walls 4a-4d, form a closed chamber 10. As best shown in FIG. 2, chamber 10 is represented by the space surrounded by the walls 4a-4d and end caps 6 and 8.

Figure 3:
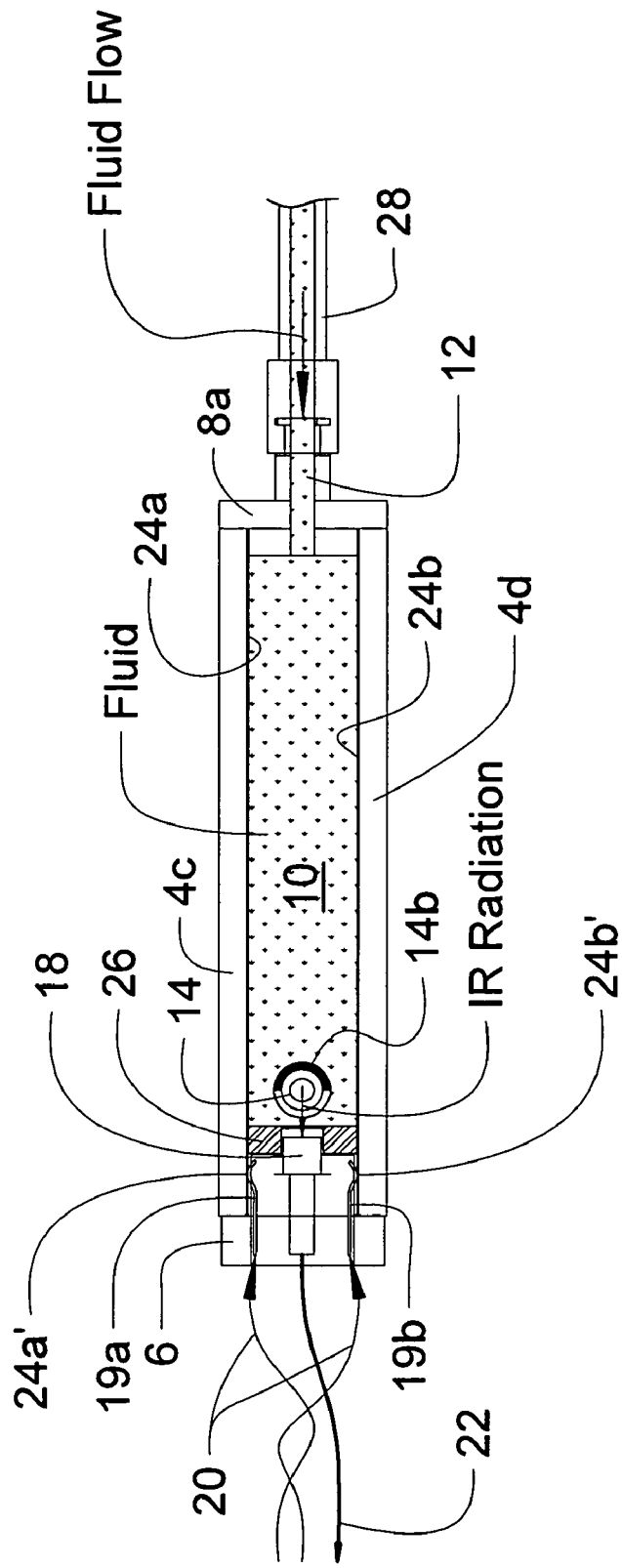
FIG. 3 is a cross-sectional view of the warmer cartridge.

There is also shown in FIGS. 1 and 2, as well as the cross sectional view of FIG. 3, an inlet luer connector 12 formed at end cap 8. An outlet luer connector 14, for the embodiment of FIGS. 1-3, is shown to extend at right angle from wall 4b. End cap 8 is configured to have an inner portion 8a that is smaller than the outer portion, so that the respective ends of walls 4a-4d may be fixedly attached to end cap 8 in the manner as shown in FIG. 3. As shown, cartridge 4 has four smooth outside surfaces along its longitudinal axis 16. Room temperature or refrigerated infusate enters the inlet or proximal connector 14 and the normothermic fluid exits from the side outlet connector 14 at the distal end of cartridge 2.

Figure 5:
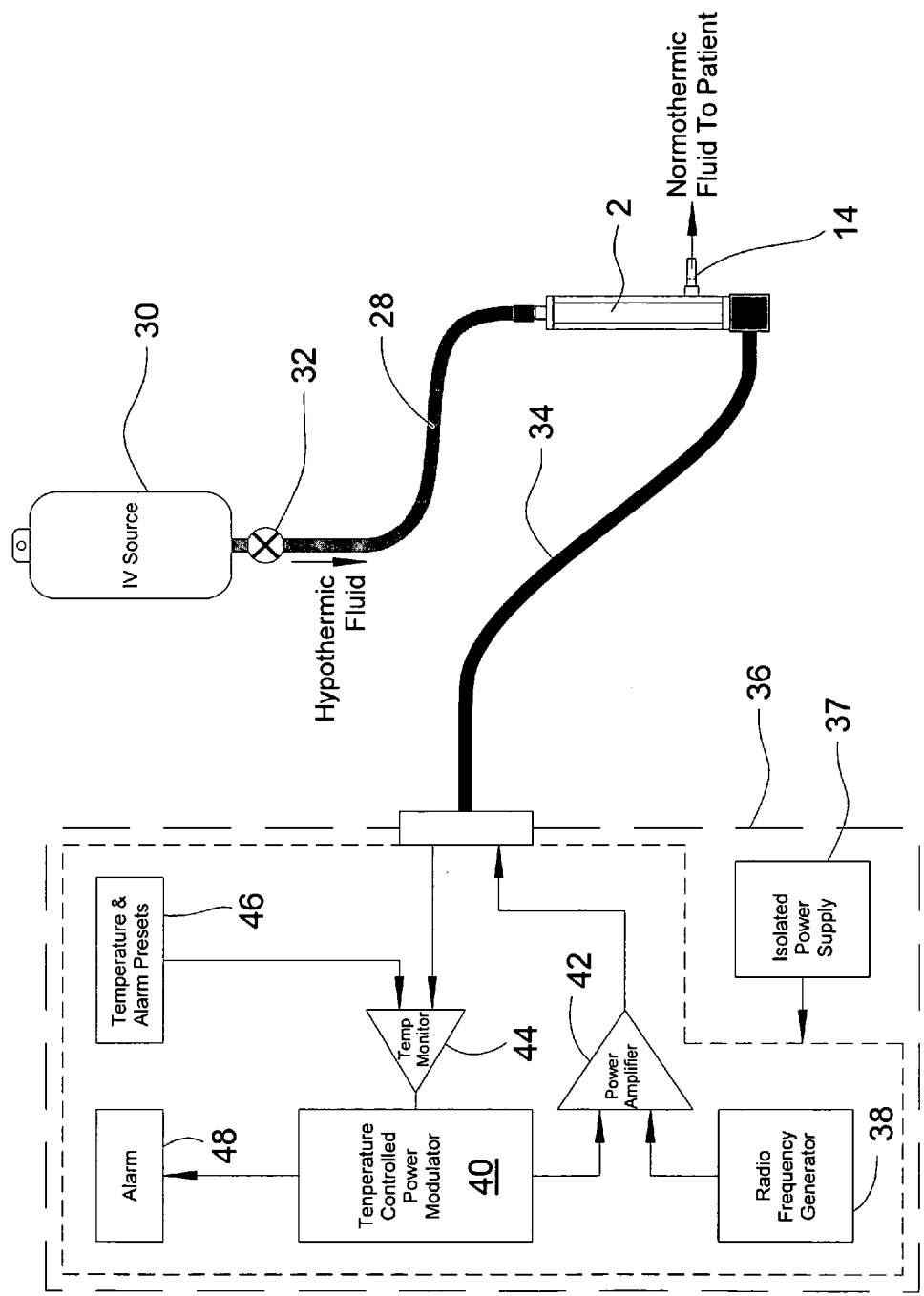
FIG. 5 shows the system of the invention which incorporates the inventive warmer cartridge of the instant invention having a single temperature monitor sensor.
Figure 6:
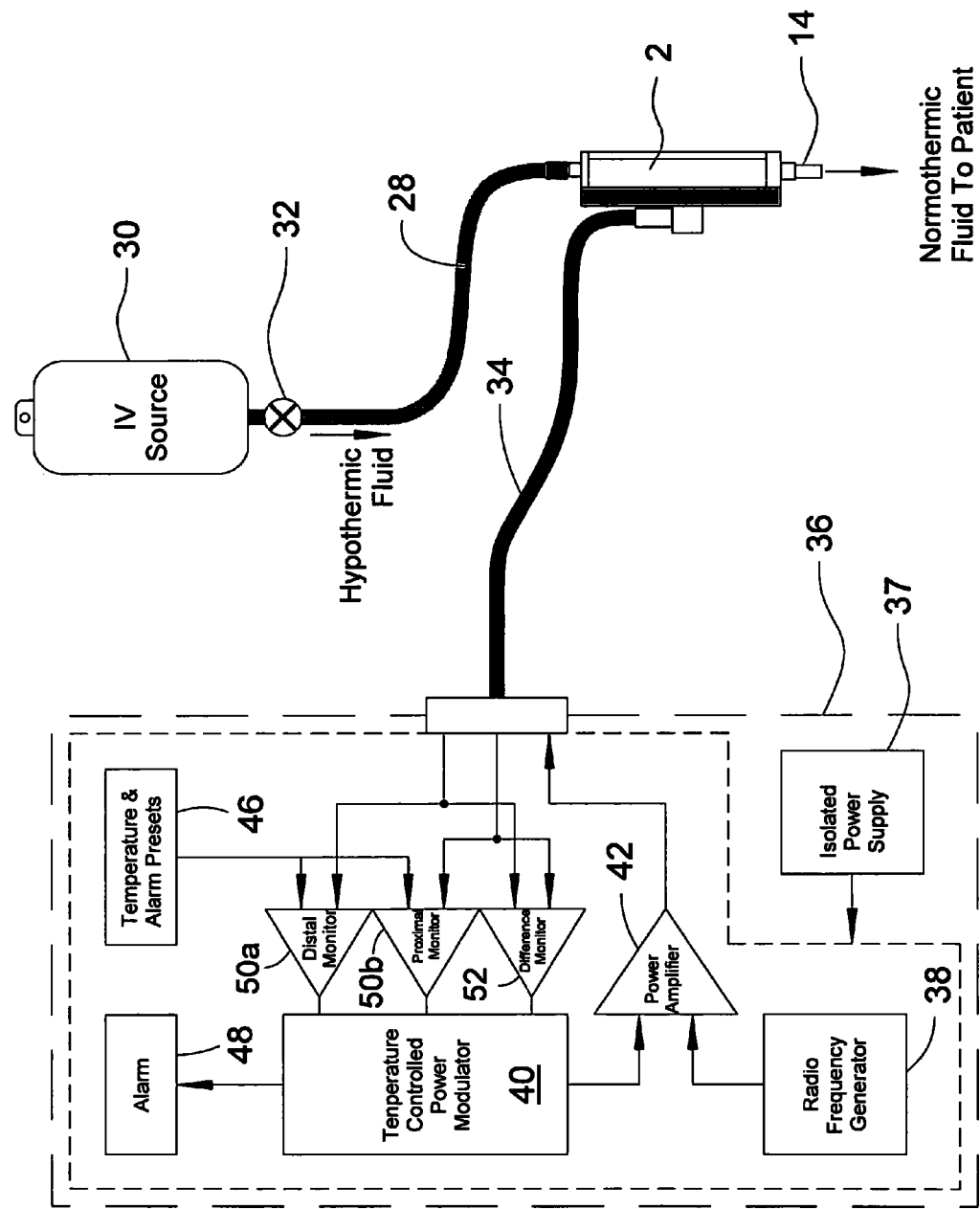
FIG. 6 is a second embodiment of the system of the invention showing the use of a plurality of monitoring sensors in the system.
Figure 7:
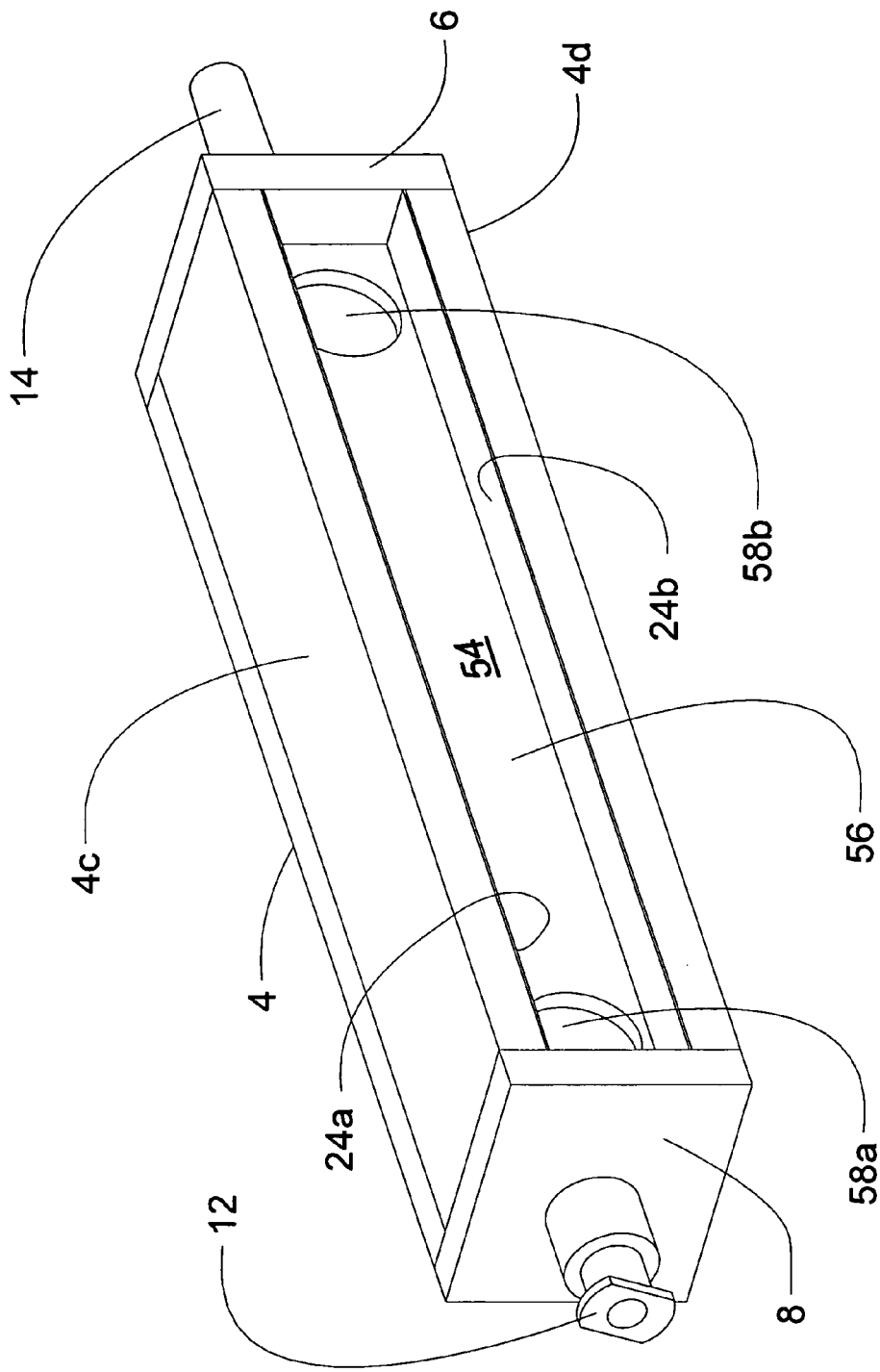
FIG. 7 shows a second embodiment of the disposable warmer cartridge of the instant invention.

The other end of cartridge 2 is closed by end cap 6, which, for the embodiment shown in FIGS. 1-3, is a connector assembly. In particular, for the embodiment of FIG. 2, end cap 6 includes an infrared (IR) sensor 18 and embedded electrical connector contacts 19a and 19b that are electrically connected by means of wires or leads 20 to a radio frequency (RF) generator, to be discussed with reference to the system shown in FIGS. 5 and 6, infra. IR sensor 18 is connected by a lead 22 to a monitoring device, also to be discussed with the overall system as shown in FIGS. 5 and 6, infra. Side guides 6b of end cap 6 ensure that end cap 6 is smoothly fitted to sidewalls 4a-4c during the assembly of cartridge 2. Sidewalls 4a-4d are made of non-conducting materials, as are end caps 6 and 8. Connector assembly or end cap 6 is removable from cartridge 2 and is reusable, while cartridge 2 is a disposable component of the system shown in FIG. 5.

Figure 4:
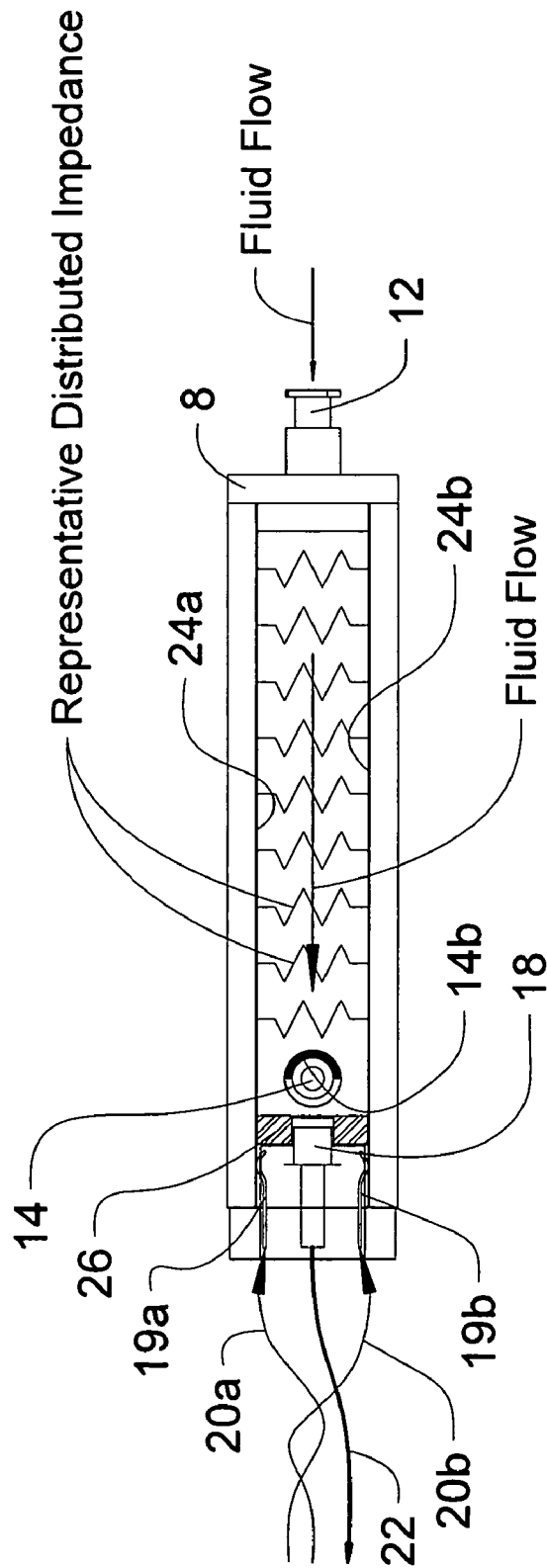
FIG. 4 is a cross-sectional view illustrating a representative distributed impedance generated between the electrodes of the warmer cartridge when an alternating electric field is established between the electrodes.

Also shown in FIG. 2 are upper electrode 24a and lower electrode 24b, which are of substantially the same dimension and are spaced substantially in parallel within chamber 10. Electrodes 24a and 24b may be made of respective layers or sheets of conductive material that are attached or bonded to the opposing walls, such as 4c and 4d, of the cartridge. Alternatively, electrodes 24a and 24b may be made from deposition of electrically conductive material or a sprayed-on metal coating to the non-conducting opposing surfaces of walls 4c and 4d. When assembled, the thin sheets of conductive electrodes are mounted to or be a part of the surfaces of opposing walls in the chamber that are facing each other. As best shown in FIGS. 3 and 4, when the cartridge is fully assembled, electrodes 24a and 24b are in electrical communication with connecter contacts 19a and 19b, respectively, at corresponding contact areas 24a' and 24b'.

Although one pair of spaced in parallel electrodes have been discussed so far, it should be appreciated that more than one pair of spaced electrodes may also be used, so long as each pair of spaced electrodes are powered by their own RF power source. Further, instead of being substantially spaced in parallel, the spaced apart electrodes may be and/or have portions thereof spaced in a non-parallel fashion, as for example at the proximal and distal portions of chamber 10.

A seal 26 is provided in chamber 10 of cartridge 2 to separate IR sensor 18 from chamber 10 proper. Seal 26 may be made of a non-conducting, infrared transparent material with an area of reduced thickness through which the sensor would read the fluid temperature of the fluid in chamber 10. As such, seal 26 may be referred to as a seal window.

As best shown in FIG. 2, a portion 14a of outlet 14 extends into chamber 10. Portion 14a has a partially hooded portion that, for the FIG. 2 embodiment, is either formed of a dark material or coated in a dark color, or otherwise referred to for this invention as having a "blackbody coating" or blackbody surface 14b. As best shown in FIGS. 3 and 4, blackbody surface 14b is positioned to face sensor 18. FIG. 3 shows in particular the relationship between IR sensor 18 and the hooded fluid outlet 14 with its blackbody coating for use with transparent fluids, if needed. FIG. 3 shows IR sensor 18 within fluid seal 26 looking through the area of reduced thickness, or its window, at the fluid medium. The fluid in chamber 10 is in intimate or direct contact with electrodes 42a and 42b.

As best shown in FIGS. 3 and 4, inlet 12 of cartridge 2 may be connected to a lumen or conduit 28 wherefrom a fluid such as for example an infusate or intravenous fluid is supplied to chamber 10. The fluid is output from chamber 10 by way of outlet 14. When an RF energy is applied to contacts 19a and 19b, and from there fed to electrodes 24a and 24b, an alternating electric field, as represented by the distributed impedance shown in FIG. 4, is generated between electrodes 24a and 24b. Given that the upper electrode 24a and lower electrode 24b are configured to have substantially the same dimension and are spaced substantially in parallel to each other, an evenly distributed impedance such as that shown in FIG. 4 is effected or established across the length of the cartridge.

As the fluid, for example the infusate or red blood cells, being fed into chamber 10 are electrically conductive electrolytes, the alternating electric field would cause the polar molecules in the fluid medium to continuously reorient themselves to face opposite poles much like the way that bar magnets behave in an alternating magnetic field. Such molecular movement causes friction between the molecules to thereby cause the fluid to rapidly heat uniformly across the length of the chamber (or along the longitudinal space between of the opposing electrodes 24a and 24b), so long as RF energy is continuously supplied to the electrodes 24. As a consequence, the fluid inside chamber 10 is directly heated. Such direct heating is turned off substantially instantaneously when the RF energy is removed. The heated fluid is output from outlet 14.

For the instant invention, as the warmer cartridge 2 is used in a medical environment, the RF frequency excitation range would be from approximately 400 KHz to 2 MHz. For the distributed impedance shown in FIG. 4, depending on the area of the electrodes and the distance between the electrodes, the impedance under RF excitation may vary from approximately 10 Ohms to 100 Ohms. If the amount of fluid in the chamber were to diminish, the impedance of the fluid would change. Therefore, by monitoring the impedance of the fluid, information may be obtained that would indicate the amount of fluid present in the chamber; and if the fluid level is deemed to be too low, then the system, as to be discussed infra, is shut off.

FIG. 5 shows a system of the instant invention with the inventive warmer cartridge of FIGS. 1-4 attached. As shown, cartridge 2 is connected to a fluid store or fluid reservoir 30 that contains infusate or intravenous fluids. The flow of the fluid from fluid store 30 may be controlled by a valve 32. The fluid is supplied to cartridge 2 by way of a conduit or lumen 28. The heated fluid outputs from outlet 14, which is connected to a conduit (not shown) and routed to the patient.

Also shown in FIG. 5 is an electrical connection or cable 34 that includes electrical leads 20a and 20b that supply the RF energy to contacts 19a and 19b, and from there to electrodes 24a and 24b. Electrical connection 34 also includes the electrical lead 22 that connects sensor 18 to the controller of the system, as represented by the controller box 36. For the system shown in FIG. 5, controller 36 includes an isolated power supply 37 and a radio frequency (RF) generator 38. There is also a temperature power modulator 40 that controls the output from RF generator 38, as amplified by power amplifier 42. As noted above, for the instant invention, the RF energy supplied to cartridge 2 for powering the electrodes may be in the range of approximately 400 KHz to 2 MHz. The amount of energy supplied to electrodes 24 is a function of how much heat to apply to the fluid in chamber 10 so that the desired temperature may be achieved for the fluid in chamber 10 of cartridge 2.

In the FIG. 5 system, controller 36 reads the temperature sensed by the infrared sensor 18 and compares it to preset temperature and alarm settings. If the measured temperature is substantially below the preset value, the power amplifier 42 applies full RF power as needed through electrical connection 34 to the pair of electrodes 24 within cartridge or heater lumen 2. As the RF power passes through the infusate fluid, the temperature rises. As the temperature approaches the preset value, the RF power is modulated to maintain the fluid at the preset temperature. Should the fluid temperature exceed the over temperature preset value, the power fed to lumen cartridge 2 is discontinued and the heating of the fluid will immediately stop, thereby preventing hemolysis.

Although an analog servo controlled system is shown in FIG. 5, it should be appreciated that a major portion of the controller system could be replaced by a microprocessor based controller that could be adapted to provide the same functions. For example, a digital based processor controller may have a microprocessor configured and programmed to perform at least the same functions as modulator 40 and temperature monitor 44. Further, in relation to the above discussed monitoring of the fluid impedance in the chamber, even though not shown in the FIG. 5 system and the further systems to be discussed, an impedance monitor such as that in the LIZ88A cardiac ablation system produced by Medical Scientific Inc. of Taunton, Mass. may be provided in the various systems to specifically monitor the impedance of the fluid in the chamber, so as to act as an additional safeguard to prevent overheating of the fluid when there is not sufficient fluid in the chamber.

Return to the preset temperature and alarm settings. To control the temperature of the heated fluid to a desired or predetermined setting, a control loop management or feedback control is needed. This is achieved by the use of sensor 18, which is an infrared (IR) sensor in the embodiment being discussed. To be able to measure the temperature of the fluid in chamber 10, in the event that the fluid is substantially transparent and therefore would not irradiate IR radiation, a surface 14b is provided inside chamber 10 and is painted or made of a material in a dark color, for example black, to create a blackbody effect so that when it is heated, IR energy that corresponds to the temperature of the fluid that heats it, i.e., the temperature of the fluid being heated in chamber 10, is irradiated to and sensed by IR sensor 18. The sensed IR energy is fed via lead 22 to controller 36 and in particular to temperature monitor 44. The received temperature is then compared with the preset high (and possibly the low) temperature, as represented in block 46. If the measured temperature is above the preset high temperature, or outside the preset range of the desired temperature, an alarm signal is sent by controller 40 to an alarm circuit 48 to warn the user that the fluid temperature is too high, or too low. If too high, it would shut off the RF heating energy. So that the measured temperature is maintained within the desired temperature range, the temperature controller 40 would modulate the amount of RF energy provided by RF generator 48 to the electrodes 24 continuously.

FIG. 6 shows a second embodiment of the system of the instant invention that uses a plurality of sensors for determining the temperature of the fluid being heated in the chamber of cartridge 2. Components that are the same as the embodiment of FIG. 5 are labeled the same. For the controller 36 of the FIG. 6 embodiment, in place of a single temperature monitor such as that shown in the FIG. 5 embodiment, a plurality of monitors are used. In brief, the system of FIG. 6 utilizes two or more infrared sensors for cartridge 2, with one being positioned to detect the fluid temperature proximate to the outlet and at least one being positioned to detect the temperature of the fluid proximate to the inlet. Either one of the sensors can control the temperature by modulating the RF power and discontinuing power in an over temperature condition. The temperature sensed by the distal sensor and the proximal sensor are output to distal monitor 50a and proximal monitor 50b, respectively. The temperature difference monitor 52 may be used to detect a diminished rate of flow or reduce the maximum allowable heating power to provide to the fluid, as the fluid is being warmed in chamber 10 of cartridge 2. As with the controller 36 shown in the FIG. 5, the analog servo control system of the FIG. 6 embodiment may also be converted to a microprocessor based system by combining the temperature power modulator 40 with the different distal, proximal and difference monitors 50 and 52.

For the FIG. 6 system, the warmer cartridge 2 of FIGS. 7-10 is utilized. In particular, cartridge 2 of the multiple sensor cartridge has a body 4 that has a recess 54 defined between upper sidewall 4c and lower sidewall 4d. The chamber of the FIG. 7 warmer cartridge further has a partition 56 that defines the back wall of recess 54. Two windows are provided at partition 56 to allow viewing into the chamber of cartridge 2. Window 58a is proximate to end cap 8 while window 58b is proximate to end cap 6. Although two windows are shown, it should be appreciated that additional windows may be provided along partition 56. As with seal window 26 in the embodiment of the cartridge shown in FIG. 2, each of windows 58a and 58b of the cartridge of the FIG. 7 embodiment also forms a barrier to the fluid chamber so that no fluid may escape from the windows.

Figure 8:
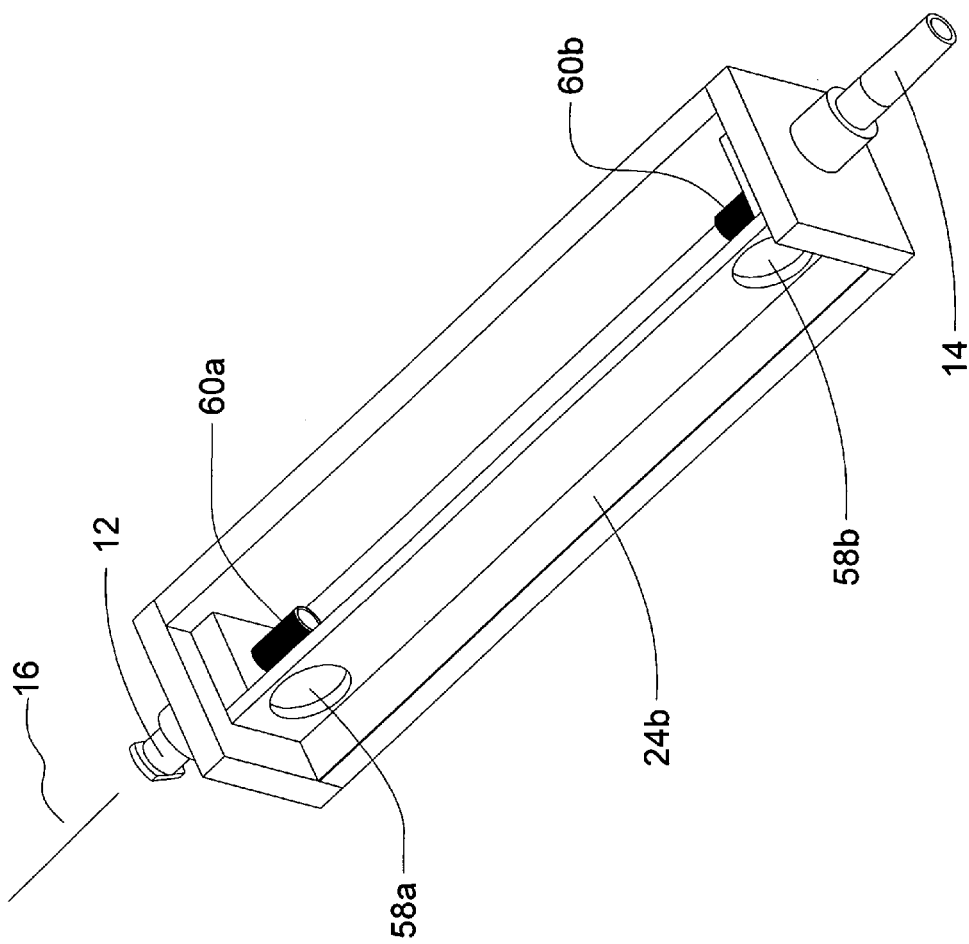
FIG. 8 shows the disposable warmer cartridge of FIG. 7 but with its top wall removed to show the IR sources by the which the respective temperatures of the fluid at the distal and proximal ends of the cartridge may be measured.

FIG. 8 shows cartridge 2 having its upper sidewall removed, so that chamber 10 is exposed. As shown, two blackbody temperature sources 60a and 60b are provided in chamber 10 in front of inlet window 58a and outlet window 58b, respectively. Same as the earlier cartridge embodiment, blackbody temperature sources 60a and 60b provide respective heated surfaces from which IR energies are radiated to the corresponding windows 58a and 58b for detection by sensors that are placed in front of those windows. By being able to detect the respective temperatures of the fluid at the inlet and outlet portions of chamber 10, any temperature difference of the fluid in chamber 10 may be monitored, and be used to determine any diminished rate of flow of the fluid or to control the amount of energy to be fed to the electrodes 24a and 24b.

Figure 9:
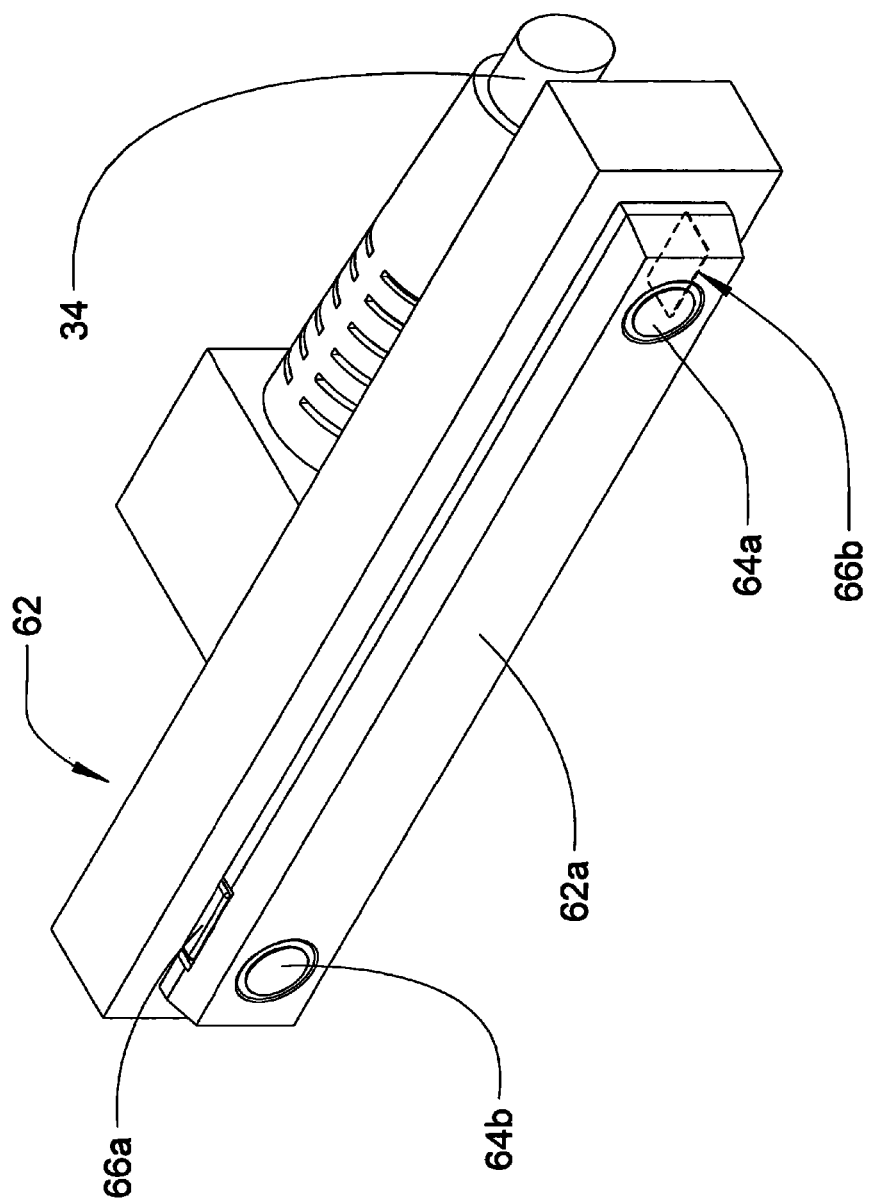
FIG. 9 shows the connector that mates to the disposable cartridge of FIG. 7.
Figure 10:
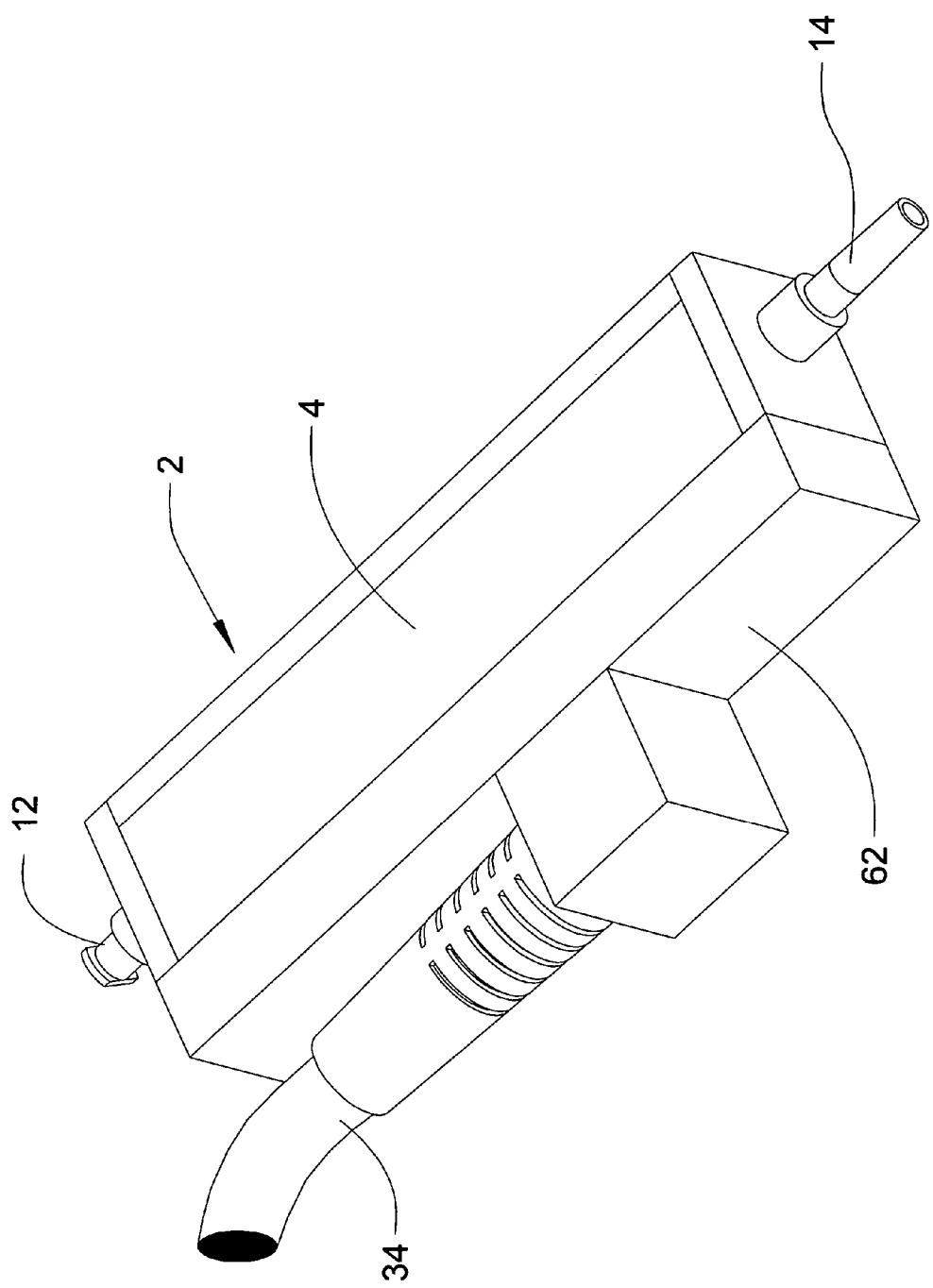
FIG. 10 is a perspective view showing the mating of a connector to the disposable warmer cartridge.

The sensors used with the cartridge shown in FIG. 8 are illustrated in FIG. 9. There, a connector 62 has an elongate connector body 62. Mounted to connector body 62 are IR sensors 64a and 64b, which are for monitoring the temperature of the fluid in chamber 10 via inlet window 58a and outlet window 58b, respectively, when connector 62 is mated to body 4 of cartridge 2, per shown in FIG. 10. Once mated to body 4, connector contacts 66a and 66b of connector 62 are in electrical contact with upper electrode 24a and lower electrode 24b, respectively, of cartridge 2, so that the electrodes 24 may be energized by the RF generator via an electrical contacts 66a and 66b. The connection of connector 62 to controller 36 is provided by connection cable 34. For the embodiment shown in FIG. 10, connector 62 is reusable while cartridge 2 remains disposable. For the system shown in FIG. 6, the signals from sensors 64a and 64b are sent to proximal monitor 50b and distal monitor 50a, respectively. The difference in those signals is measured by difference monitor 52. Such difference may be used by temperature controller 40 to control the modulation of the RF energy to be provided to the electrodes 24a and 24b for controlling the heating of the fluid in the chamber of the warmer cartridge 2.

The sensors discussed so far are IR-sensors that do not come into contact with the fluid being heated in the chamber of the warmer cartridge. Those sensors are non-contact sensors. The sensors discussed hereinbelow with reference to FIGS. 11-17 are sensors that are in intimate or direct contact with the fluid being heated in the chamber of the cartridge. Such direct contact sensing method requires the sensors be thermistors or RTDs (resistance temperature detectors) that are part of the disposable cartridge, with an electrical connector plug for the thermistors as well as for power. The thermistors must be of the position interchangeable type. One such exemplar thermistor is a Honeywell Uni-Curve thermistor made by the Honeywell company. The RTDs are conventional RTD sensors.

Figure 11:
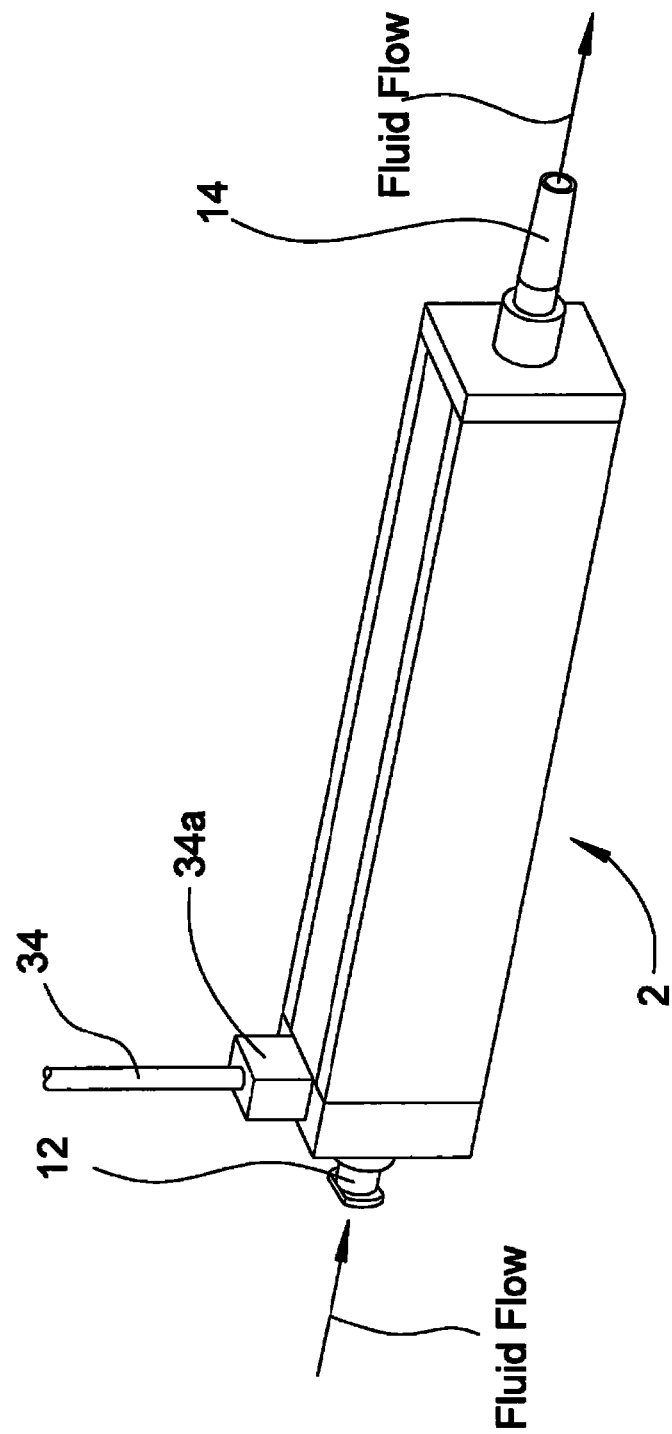
FIG. 11 is an illustration of a third embodiment of the warmer cartridge of the instant invention.

With reference to FIG. 11, an assembled disposable cartridge 2 that has direct contact sensors is shown to be connected to an interconnecting cable 34. As shown in the exploded view of FIG. 12, the connector 32a of cable 34 is connectable to the proximal end cap 8 by way of pin contacts 68. Similar to the earlier embodiment, cartridge 2 of FIG. 12 has non-conductive four walls 4a-4d for defining a chamber 10. The ends of the chamber 10 are defined by proximal end cap 8 as well as distal end cap 6. Inlet luer 12 is provided at end cap 8 while outlet luer 14 is provided at end cap 6. A pair of opposing electrodes 24a and 24b are attached or bonded to top wall 4c and bottom wall 4d, respectively. As before, upper and lower electrodes 24a and 24b are of substantially the same dimension and are spaced substantially in parallel with each other so that a distributed alternating electric field is generated or established between the electrodes, when the electrodes are energized with RF energy from an RF generator.

Figure 12:
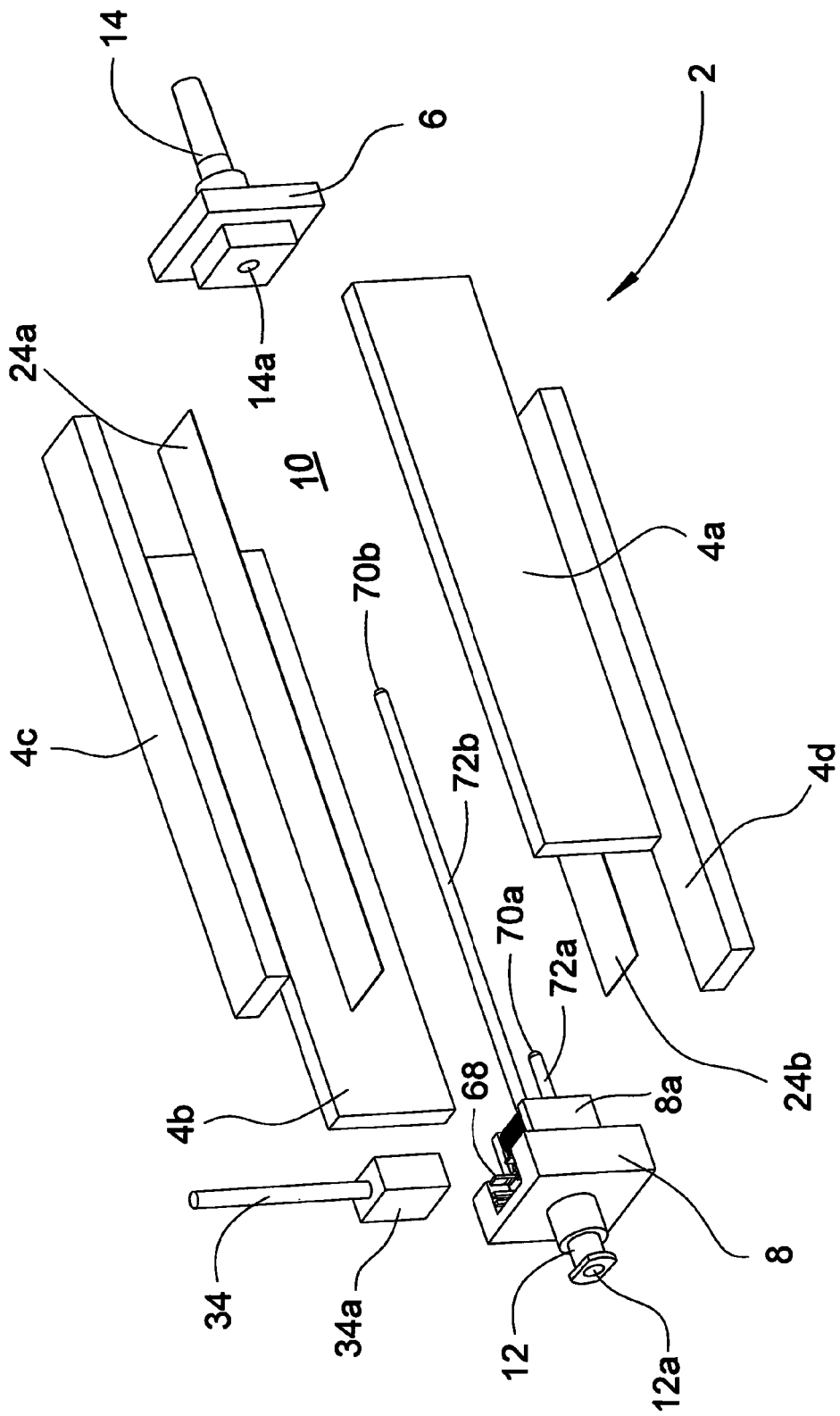
FIG. 12 is an exploded view of the various components that made up the warmer cartridge of FIG. 11.
Figure 13:
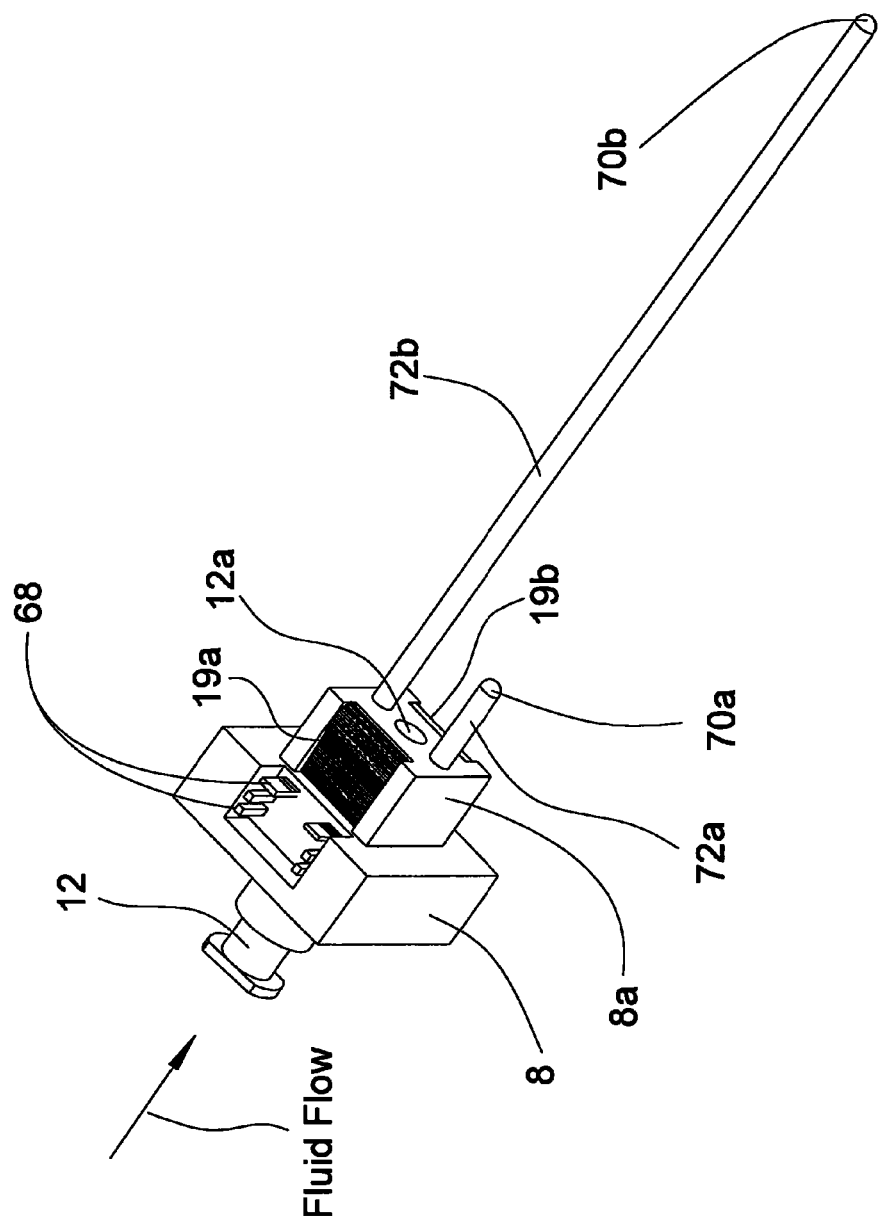
FIG. 13 shows the end cap of the FIG. 11 warmer cartridge with the sensors and the electrical pin connectors to the electrodes being shown.

For the cartridge of FIG. 12, end cap 8, as best shown in FIG. 13, has at its portion 8a, in addition to the upper and lower electrode connectors 19a and 19b, thermistor type sensors 70a and 70b extending therefrom. Sensors 70a and 70b are protected by corresponding sensor sheaths 72a and 72b, with the actual sensors being exposed or embedded in a thermally conductive material at the respective tips of sensor sheaths 72a and 72b.

Alternatively, sheaths 72a and 72b may each be close ended with their respective distal ends where sensors 70a and 70b otherwise would have extended through protected by a heat conductive shroud cover so that sensors 70a and 70b are not exposed to the fluid in the chamber but are nonetheless adaptable to measure the temperature of the fluid in the chamber. For this embodiment, a through hole is provided in end cap 8 to communicate with each sheath 72 so that a thermistor or RTD sensor may be inserted into the protective sheath to conductively measure the temperature of the fluid in the chamber via the shroud cover when needed. After measurement, the sensor is removed and can be further used in another similarly designed disposable heater cartridge.

In the event that only one temperature measurement needs to be taken in the chamber, only one sheath 72 and a thermistor or RTD sensor that mates thereinto are used. Thus, although two sensors 70 and their protective sheaths 72 are shown in FIG. 12, it should be appreciated that, to measure the temperature of the fluid in the chamber, if there is no desire to measure variants of the temperature of the fluid in the chamber, only one sensor 70 protected by a sheath 72 is needed.

For the cartridge of FIG. 12, fluid is input to input luer connector 12, and from there through inlet opening 12a into chamber 10. The output of fluid that has been heated in chamber 10 is output through outlet hole 14a, and outlet luer connector 14, to the patient. See also the fluid flow path shown in FIG. 15.

Figure 14:
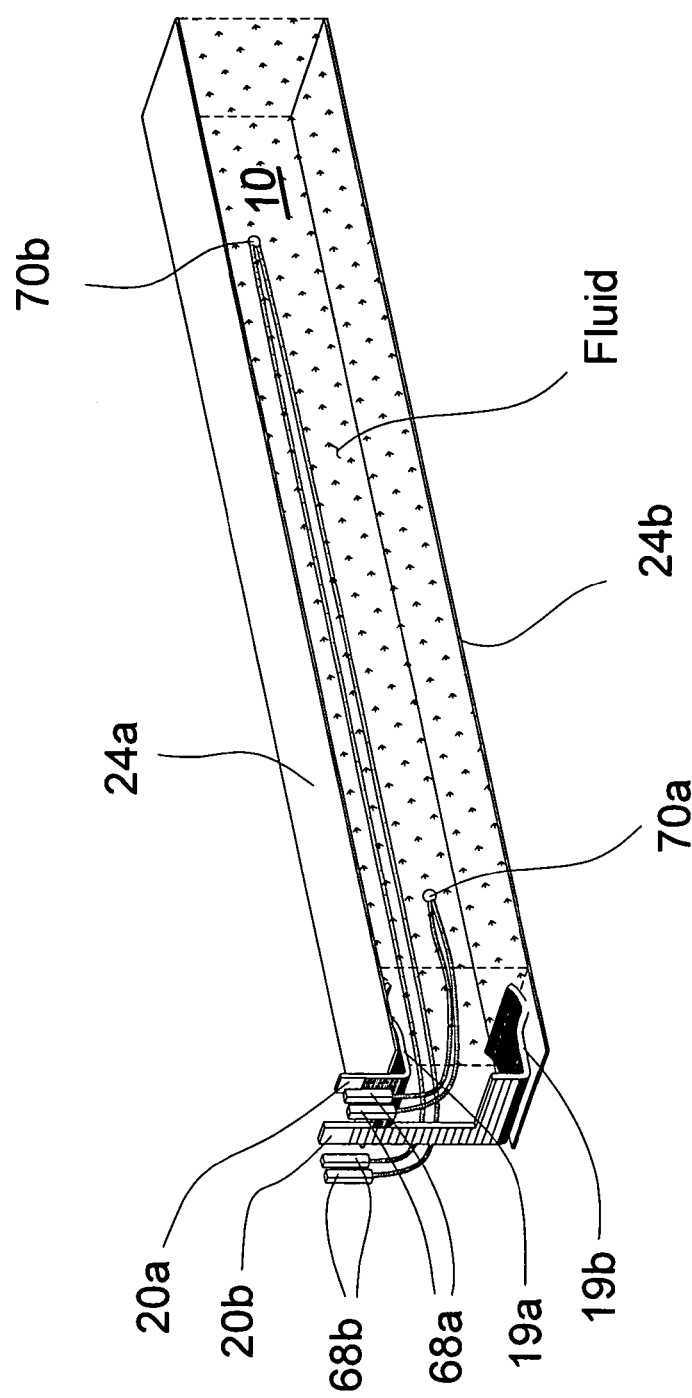
FIG. 14 is an exposed perspective view showing the unsheathed sensors and the electrical connectors to the electrodes.

Shed of the non-essential components, for example the sensor sheaths 72 that protect the sensor wires and the walls 4 of cartridge 2, FIG. 14 illustrates exemplar positioning of the inlet sensor 70a and outlet sensor 70b, with reference to chamber 10 as defined by upper electrode 24a and lower electrode 24b. Instead of one sensor positioned proximate to the outlet portion of chamber 10, there may in practice be additional sensors placed thereat or throughout the length of chamber 10, if it is desirable to monitor the different temperatures of the fluid being heated along the length of the chamber, as affected by the fluid flow.

In particular, FIG. 14 shows the relationship of sensors 70a and 70b with their respective sets of connectors 68a and 68b. Also being shown in FIG. 14 are the upper electrode connector 20a and lower electrode connector 20b, and their corresponding contacts with upper electrode 24a and lower electrode 24b, respectively. The fluid flows from the inlet sensor end to the outlet sensor end, with the fluid being heated as RF power is provided to electrodes 24 to establish or effect an alternating electric field to thereby heat the fluid between the electrodes. In normal operation, the inlet sensor would be cooler than the outlet sensor, as the fluid at the inlet is heated less than the fluid at the outlet portion of the chamber. The faster the flow of the fluid, the greater the difference between the two. And as the flow is reduced, the difference between the respective temperatures at the inlet and outlet portions of the chamber diminishes. When the flow stops, the difference would approach or pass through zero, thereby providing controller 38 the data or information necessary to determine the stoppage of the fluid flow.

Figure 15:
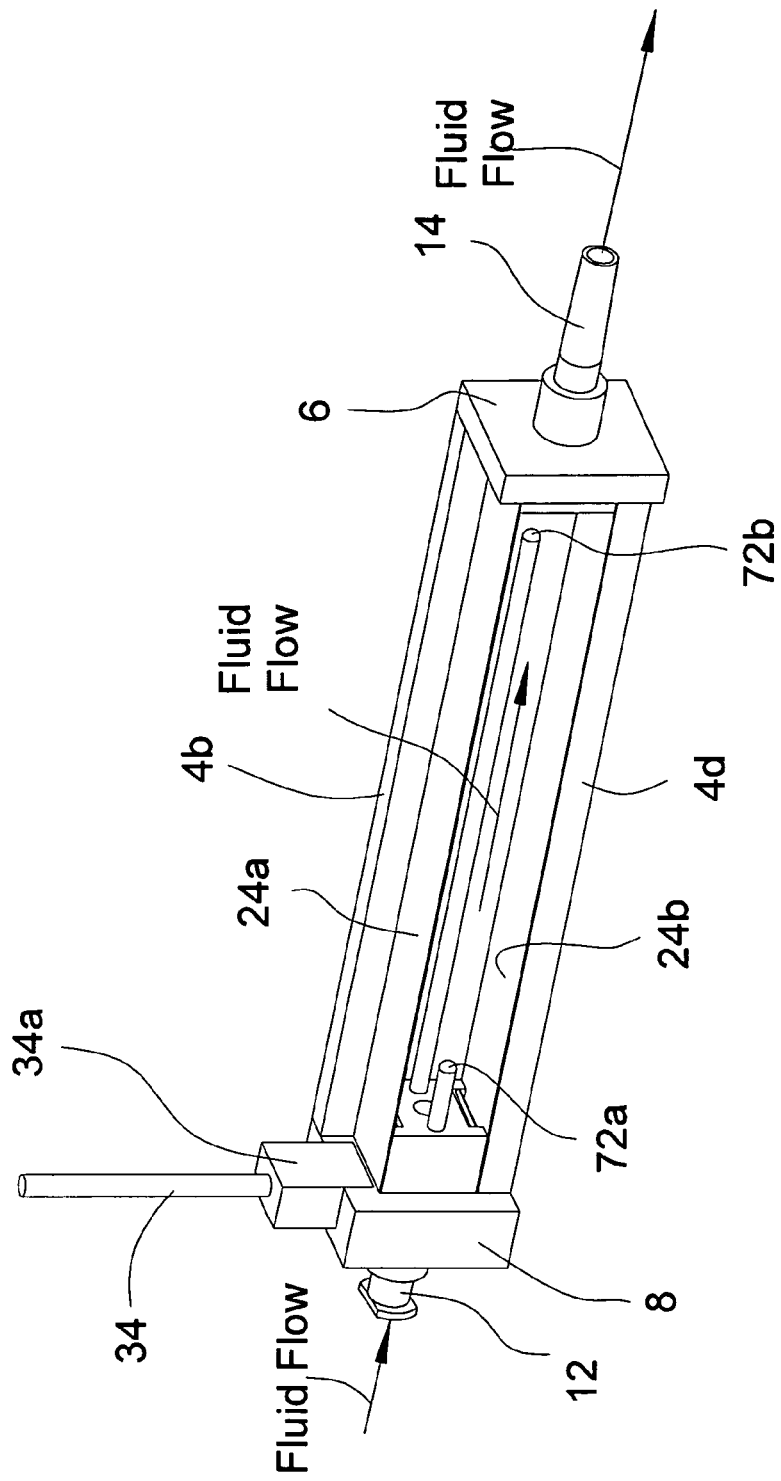
FIG. 15 is a perspective view of the third embodiment cartridge with one sidewall of the cartridge removed to show the placement of the sensors in the chamber of the cartridge.

FIG. 15 shows the assembled relationship of the different components of the direct sensor contact warmer cartridge, with front wall 4a and top wall 4c removed.

Figure 16:
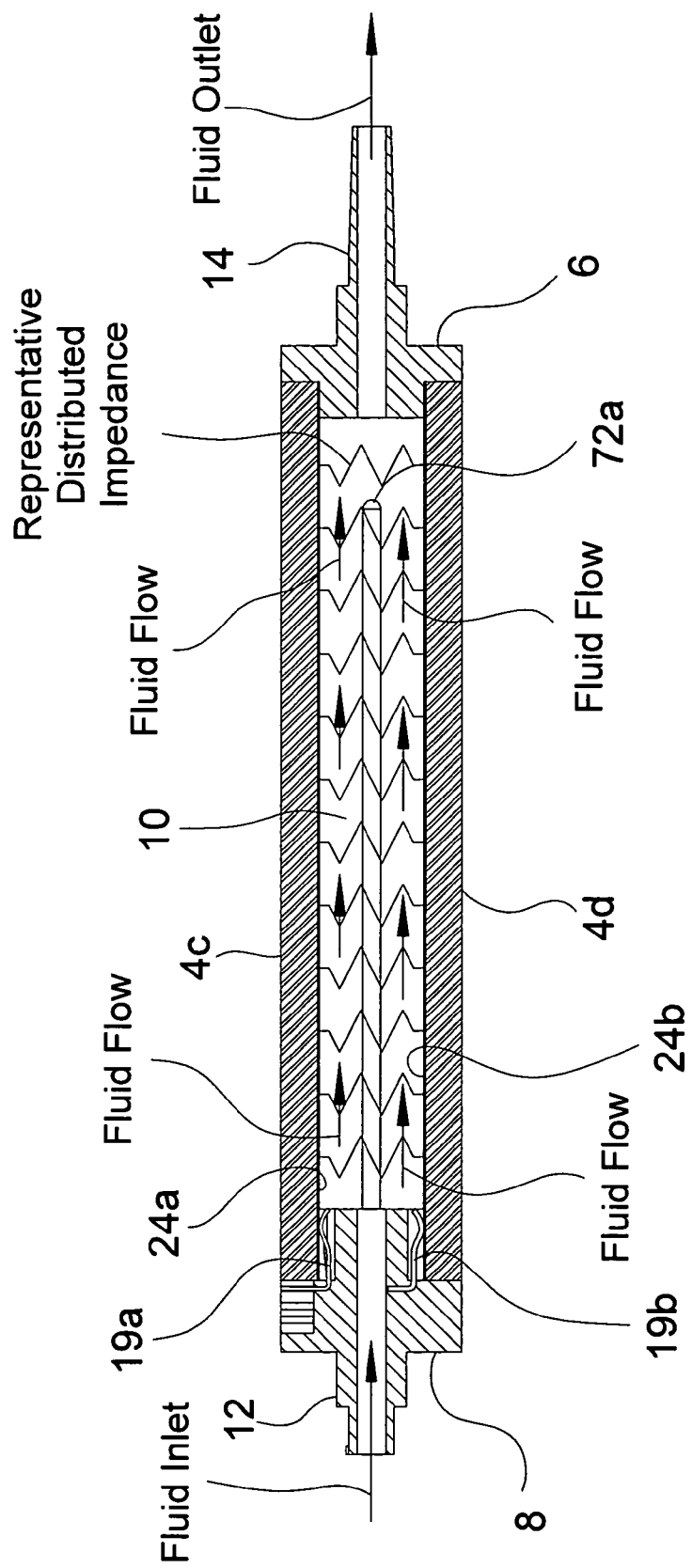
FIG. 16 is a cross-sectional view illustrating the representative distributed impedance in the chamber of the third embodiment cartridge when the electrodes are energized.

FIG. 16 shows a cut-away view of the disposable cartridge with the dual sensors. The infusate fluid is shown to flow from inlet 12 to outlet 14, with the fluid being heated by the alternating electric field, shown as a representative distributed impedance, generated between upper electrode 24a and lower electrode 24b. For the exemplar warmer cartridge, depending on the area of the electrodes and the distance between them, the impedance under RF excitation may vary from approximately 10 Ohms to 100 Ohms.

Figure 17:
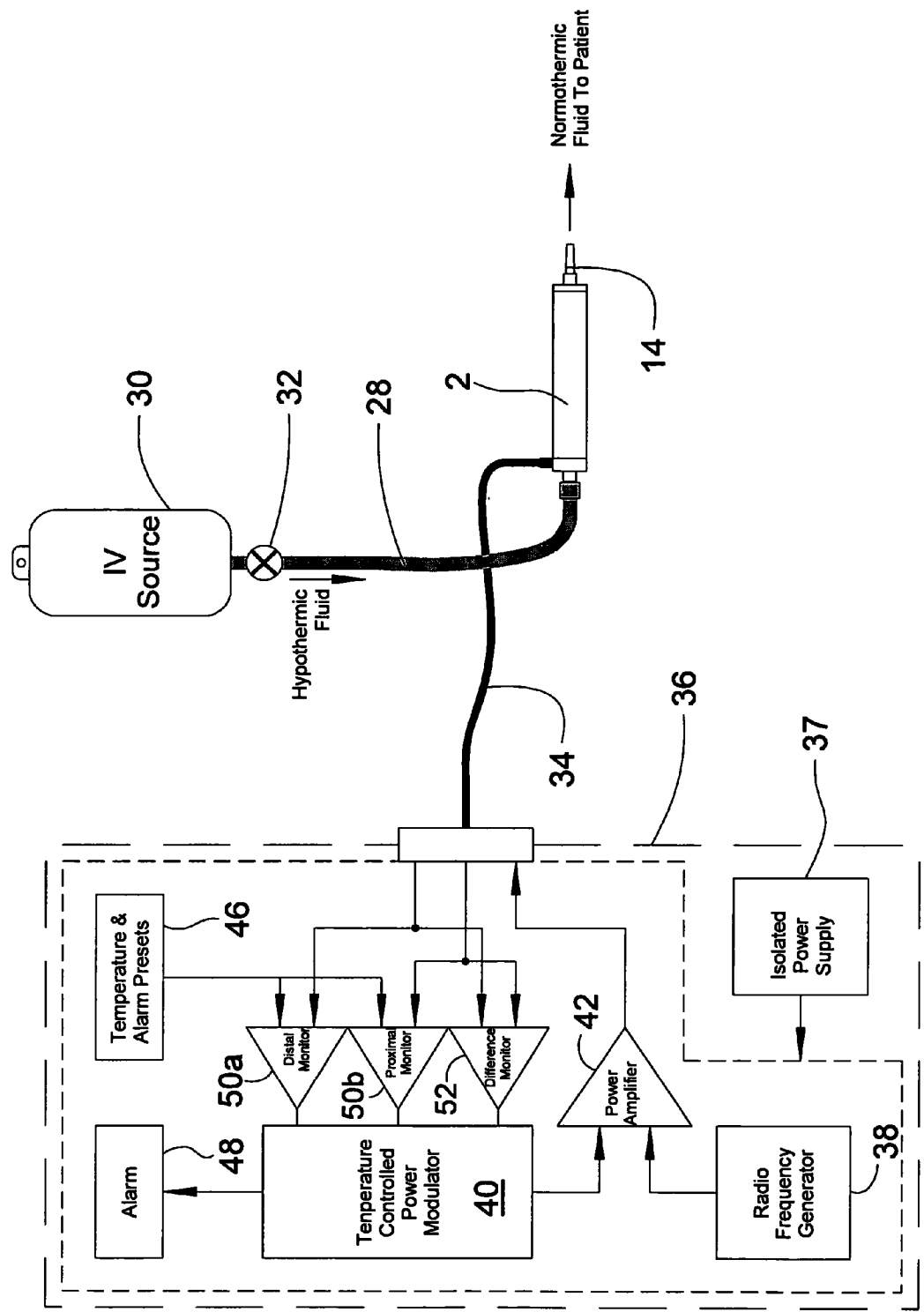
FIG. 17 illustrates a system of the invention that utilizes the third embodiment warmer cartridge of the instant invention.

The controller system for the direct contact sensor embodiment illustrated in FIGS. 12-16 is shown in FIG. 17. As two direct contact sensors are used, the controller system of FIG. 17 is the same as the controller system of FIG. 6. The difference being that the system of FIG. 6 deals with non-direct contact sensors, i.e., of IR sensors, whereas the system of FIG. 17 utilizes two direct contact sensors, one positioned to detect the inlet temperature and another one positioned to detect the outlet temperature. As before, if the measured temperature is below a preset temperature value, the power amplifier 42 would apply full RF power as needed through cable 34 to electrodes 24a and 24b of the cartridge for heating the fluid in the chamber. As the RF power passes through the fluid in the chamber, the temperature of the fluid rises. As the temperature approaches the preset value, the RF power is modulated to maintain the fluid at the preset temperature. Should the fluid temperature exceed the over temperature preset value, the power supplied to the electrodes in the cartridge is discontinued, and heating will immediately stop, thereby preventing hemolysis. Either one of the two sensors 72a and 72b may be used to control the temperature by modulating the RF power and discontinuing the power in an over temperature condition, with the data being sent to the distal and proximal monitors 50a and 50b. The temperature difference monitor 52 is used to detect a diminished rate of flow, air in the luer and/or to reduce the maximum available heating power as the infusate fluid in the delivery conduit warms. As before, the temperature power modulator 40 and the analog monitors may be replaced by a microprocessor, which may be programmed to provide the same functions.

The invention claimed is:

1. Apparatus for warming infusate or intravenous fluids for use by a patient, comprising:
   a radio frequency (RF) generator adapted to output a RF energy;
   a fluid store;
   a body having an enclosed chamber extending along a longitudinal axis with an inlet and an outlet, a fluid from said fluid store for treatment of a patient passing into said chamber through the inlet and out of said chamber through the outlet, at least one pair of electrodes spaced apart substantially in parallel along the longitudinal axis within said chamber electrically connected to said generator, said electrodes selectively powered by RF energy from said generator for effecting an electric field between said electrodes to cause direct heating of the fluid entering into said chamber through the inlet and passing between said spaced apart electrodes along the length of said chamber before exiting through the outlet; and a temperature regulating system communicatively connected to said body for sensing the temperature of the fluid in said chamber and for controlling the RF energy supplied to said electrodes to maintain the fluid in said chamber at a desired temperature.

2. Apparatus of claim 1, wherein said electrodes comprise two substantially parallel conductive planes having substantially the same dimension at opposing surfaces of said chamber, wherein when RF energy is fed to said conductive planes by said generator, an alternating electric field is created between said conductive planes to heat the fluid in the chamber.

3. Apparatus of claim 1, wherein said electrodes comprise respective films of conductive material deposited as respective coatings in substantially the same dimension onto opposing surfaces along the longitudinal axis of said chamber so that the fluid in said chamber is heated evenly substantially along the length of said chamber when said films are energized by said generator.

4. Apparatus of claim 1, wherein said electrodes comprise respective layers or sheets of conductive material of substantially the same dimension attached to opposing surfaces of said chamber so that more than one pair of space apart electrodes are provided within said chamber.

5. Apparatus of claim 1, wherein said temperature regulating system comprises at least one sensor for sensing the temperature of the fluid in said chamber without contacting the fluid, said sensor being an IR sensor that detects the IR energy radiating from a heated surface in said chamber, the radiated IR energy corresponding to the temperature of the fluid.

6. Apparatus of claim 1, wherein said temperature regulating system comprises at least one sensor positioned within said chamber for measuring the temperature of the fluid in said chamber.

7. Apparatus of claim 1, wherein said temperature regulating system comprises a distal sensor and a proximal sensor each extending from one end of said body into said chamber and be in contact with the fluid for measuring the temperatures at the distal and proximal locations, respectively, in said chamber.

8. Apparatus of claim 1, wherein said temperature regulating system comprises at least one sensor positioned in said chamber for sensing the temperature of the fluid in said chamber, said sensor being separated from the fluid by a protective cover.

9. Apparatus of claim 5, wherein said sensor is either positioned at one end of said body so as to focus into said chamber along the longitudinal axis of said chamber or positioned along one side of said body so as to focus into said chamber orthogonal to the longitudinal axis of said chamber.

10. Apparatus of claim 1, wherein said temperature regulating system comprises a plurality of sensors each positioned at a side of said body for sensing respective temperatures of the fluid along said chamber without contacting the fluid, each of said sensors being an IR sensor that detects the IR energy radiating from a corresponding heated surface in said chamber orthogonal to the longitudinal axis of said body.

11. Apparatus of claim 1, wherein said temperature regulating system comprises at least one sensor for sensing the temperature of the fluid in said chamber, said sensor being positioned at one end of said chamber and is removable from said body, a seal separating said sensor from said chamber so that said sensor is not in contact with the fluid in said chamber.

12. Apparatus of claim 1, wherein said generator is adapted to energize said electrodes with a RF energy anywhere in the range from approximately 400 KHz to 2 MHz.

13. A disposable warmer for heating fluids to be infused to a patient, comprising: an elongate body having an enclosed chamber with an inlet and an outlet through which a fluid respectively passes into and out of the chamber, said body non-permanently connectable to a fluid store at its inlet to enable the fluid in the fluid store to flow into said chamber and non-permanently connectable to a conduit at its outlet to supply the fluid to the patient; and at least one pair of electrodes having substantially the same dimension provided within said chamber longitudinally along the length of opposing inside walls of said chamber, the pair of electrodes being spaced apart and each extending longitudinally in parallel to the other along a corresponding opposing inside wall of said chamber, said electrodes adapted to be electrically energized by a radio frequency (RF) energy from a RF generator to effect a substantially evenly distributed alternating electric field between the electrodes along the length of said chamber for heating the fluid in said chamber along the length of said electrodes.

14. Warmer of claim 13, wherein said electrodes comprise respective films of conductive material deposited on onto the substantially parallel surfaces of the opposing inside walls of said chamber.

15. Warmer of claim 13, wherein said electrodes comprise respective layers or sheets of conductive material attached to the surfaces of the substantially in parallel to opposing inside walls that extend longitudinally along said chamber.

16. Warmer of claim 13, further comprising at least one sensor for sensing the temperature of the fluid in said chamber without contacting the fluid, said sensor being an IR sensor that detects the IR energy radiating from a heated surface in said chamber, the radiated IR energy corresponding to the temperature of the fluid.

17. Warmer of claim 13, further comprising at least one sensor positioned within said chamber for measuring the temperature of the fluid in said chamber.

18. Warmer of claim 13, further comprising a distal sensor and a proximal sensor each extending from one end of said body into said chamber and be in contact with the fluid for measuring the temperatures at the distal and proximal locations, respectively, in said chamber.

19. Warmer of claim 13, further comprising at least one sensor for sensing the temperature of the fluid in said chamber, said sensor being positioned either at one or both ends, or at any side of said chamber, a seal separating said sensor from said chamber so that said sensor is not in contact with the fluid in said chamber.

20. Warmer of claim 13, wherein said electrodes are energized by said generator with a radio frequency energy anywhere in the range from approximately 400 KHz to 2 MHz.

21. A method of infusing a temperature controlled fluid to a patient to prevent hypothermia in the patient, comprising the steps of:

a) forming an elongate body having an enclosed chamber with an inlet and an outlet;

b) providing at least one pair of spaced apart electrodes longitudinally along opposing inside walls of said chamber to form a pair of substantially in parallel electrically conductive planes inside said chamber;

c) electrically connecting said electrodes to a radio frequency (RF) generator;

d) connecting the inlet of said body to an output of a fluid store that contains a fluid to be infused to the patient to enable the fluid in the fluid store to flow into said chamber;

e) supplying power from said RF generator to said electrodes to effect an alternating electric field between said pair of electrically conductive parallel planes to heat the fluid in said chamber; and f) connecting the outlet of said body to a conduit in fluid communication with the patient so that the heated fluid in the chamber may be output to the patient.

22. Method of claim 21, wherein step b further comprises the step of:

depositing respective films of conductive material of substantially the same dimension onto the respective surfaces of the longitudinal opposing inside walls of said chamber so that a substantially evenly distributed alternating electric field is effected between said electrodes to heat the fluid in said chamber when said films are energized by said generator.

23. Method of claim 21, wherein step b further comprises the step of:

attaching respective layers or sheets of conductive material of substantially the same dimension to the surfaces of the opposing inside walls of said chamber so that a substantially evenly distributed alternating electric field is effected between the respective layers to evenly heat the fluid in said chamber when said respective layers or sheets are energized by said generator.

24. Method of claim 21, further comprising the step of:

providing said body with at least one sensor for sensing the temperature of the fluid in said chamber without contacting the fluid, said sensor being an IR sensor that detects the IR energy radiating from a heated surface in said chamber, the radiated IR energy corresponding to the temperature of the fluid.

25. Method of claim 21, further comprising the step of:

positioning at least one sensor within said chamber for measuring the temperature of the fluid in said chamber.

26. Method of claim 21, further comprising the step of:

extending a distal sensor and a proximal sensor from one end of said body into said chamber to be in contact with the fluid for measuring the temperatures at the distal and proximal locations, respectively, in said chamber.

27. Method of claim 21, further comprising the steps of:

positioning at least one sensor for sensing the temperature of the fluid in said chamber either at one or both ends, or at any side of said chamber; and separating said sensor from said chamber with a seal so that said sensor is not in contact with the fluid in said chamber.

28. Method of claim 21, wherein step e comprises the step of:

energizing said electrodes with a RF energy anywhere in the range from approximately 400 KHz to 2 MHz.

29. Method of claim 21, wherein said step b comprises the step of:

spacing said electrodes in said chamber substantially in parallel to each other.

30. Method of claim 25, further comprising the step of:

separating said one sensor from the fluid in said chamber with a protective cover so that said sensor measures the temperature of the fluid through the protective cover.

* * * * *